US006388062B1

(12) United States Patent
Halazonetis et al.

(10) Patent No.: US 6,388,062 B1
(45) Date of Patent: May 14, 2002

(54) MODIFIED P53 TETRAMERIZATION DOMAINS HAVING HYDROPHOBIC AMINO ACID SUBSTITUTIONS

(75) Inventors: Thanos D. Halazonetis; Elena S. Stavridi, both of Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 09/305,914

(22) Filed: May 5, 1999

Related U.S. Application Data

(60) Provisional application No. 60/084,839, filed on May 8, 1998.

(51) Int. Cl.[7] .......................... C07H 21/02; C07H 21/04; C07K 1/00; C07K 14/00
(52) U.S. Cl. ..................... 536/23.4; 536/23.1; 536/23.5; 530/350; 530/827
(58) Field of Search ............................... 435/69.1, 70.1, 435/455; 514/2, 44; 530/350, 827; 536/23.1, 23.4, 23.5

(56) References Cited

U.S. PATENT DOCUMENTS

| | | | |
|---|---|---|---|
| 5,362,623 A | 11/1994 | Vogelstein et al. | 435/6 |
| 5,573,925 A | 11/1996 | Halazonetis | 435/69.7 |
| 5,721,340 A | 2/1998 | Halazonetis | 431/357 |
| 5,847,083 A | 12/1998 | Halazonetis | 530/358 |

FOREIGN PATENT DOCUMENTS

| | | |
|---|---|---|
| WO | WO 95/17213 | 6/1995 |
| WO | WO 96/16989 | 6/1996 |
| WO | WO 97/10853 | 3/1997 |
| WO | WO 98/31703 | 7/1998 |

OTHER PUBLICATIONS

Ledley, Pharmaceutical Approach to Somatic Gene Therapy, Pharmaceutical Research, vol. 13, No. 11, Nov. 1996, pp. 1595–1614.*
Verma et al., Gene therapy promises, problems and prospects, Nature, vol. 189, Sep. 18, 1997, pp. 239–242.*
Rosenberg et al., Gene Therapist, Heal Thyself, Science, vol. 287, Mar. 10, 2000, p. 17.*
W. Maltzman and L. Czyzyk, "UV Irradiation Stimulates Levels of p53 Cellular Tumor Antigen in Nontransformed Mouse Cells," *Mol. Cell. Biol.,* 4:1689–1694 (Sep. 1984).
M. B. Kastan et al., "Participation of p53 Protein in the Cellular Response to DNA Damage," *Cancer Res.,* 51:6304–6311 (Dec. 1, 1991).
S.W. Lowe et al., "p53–Dependent Apoptosis Modulates the Cytotoxicity of Anticancer Agents," *Cell,* 74:957–967 (Sep. 24, 1993).
S.W. Lowe et al., "p53 is Required for Radiation–Induced Apoptosis in Mouse Thymocytes," *Nature,* 362:847–849 (Apr. 29, 1993).

A.R. Clarke et al., "Thymocyte Apoptosis Induced by p53–Dependent and Independent Pathways," *Nature,* 362:849–852 (Apr. 29, 1993).
A. D. Leonardo et al., "DNA Damage Triggers a Prolonged p53–Dependent $G_1$ Arrest and Long–Term Induction of Cip1 in Normal Human Fibroblasts," *Genes Dev.,* 8:2540–2551 (Nov. 1, 1994).
S. Fields and S.K. Jang, "Presence of a Potent Transcription Activating Sequence in the p53 Protein," *Science,* 249:1046–1049 (Aug. 31, 1990).
N.P. Pavletich et al., "The DNA–Binding Domain of p53 Contains the Four Conserved Regions and the Major Mutation Hot Spots," *Genes Dev.,* 7:2556–2564 (Dec. 1993).
P. Wang et al., "p53 Domains: Structure, Oligiomerization, and Transformation," *Mol. Cell. Biol.,* 14:5182–5191 (Aug. 1994).
Y. Wang et al., "p53 Domains: Identification and Characterization of Two Autonomous DNA–Binding Regions," *Genes Dev.,* 7:2575–2586 (Dec. 1993).
H.W. Stürzbecher et al., "A C–Terminal a–helix Plus Basic Region Motif is the Major Structural Determinant of p53 Tetramerization," *Oncogene,* 7:1513–1523 (Jun. 1992).
H. Sakamoto et al., "Specific Sequences from the Carboxyl Terminus of Human p53 Gene Product form Anti–Parallel Tetramers in Solution," *Proc. Natl. Acad. Sci. USA,* 91:8974–8978 (Sep. 1994).
Pietenpol et al., "Sequence–Specific Transcriptional Activation is Essential for Growth Suppression by p53," *Proc. Natl. Acad. Sci. USA,* 91:1998–2002 (Mar. 1994).
C. C Harris, "p53: At the Crossroads of Molecular Carcinogenesis and Risk Assessment," *Science,* 262:1980–1981 (Dec. 24, 1993).
S. Friend, "p53: A Glimpse at the Puppet Behind the Shadow Play," *Science,* 265:334–335 (Jul. 15, 1994).

(List continued on next page.)

Primary Examiner—Deborah Crouch
Assistant Examiner—Joseph T. Woitach
(74) Attorney, Agent, or Firm—Howson and Howson

(57) ABSTRACT

Modified p53 tetramerization domains which do not hetero-oligomerize with native p53 tetramerization domains are described. These modified p53 tetramerization domains have one or more of the following substitutions in the region of residues 325 to 355 of human p53: Leu330 substituted with Phe; Met340 substituted with Phe; Ala347 substituted with Ile; Leu348 substituted with Met; Ala353 substituted with Leu; Gln354 substituted with Leu; Ala355 substituted with Asp. Also described are p53 proteins containing these modified p53 tetramerization domains linked to a p53 DNA binding domain. These proteins and the nucleic acid sequences encoding them, are useful in ameliorating conditions associated with inappropriate p53 function.

11 Claims, No Drawings

OTHER PUBLICATIONS

J. Bargonetti et al., "A Proteolytic Fragment from the Central Region of p53 has Marked Sequence–Specific DNA–Binding Activity When Generated from Wild–type but not from Oncogenic Mutant p53 Protein," *Genes Dev.,* 7:2565–2574 (Dec. 1993).

J. Bargonetti et al., "Wild–Type but not Mutant p53 Immunopurified Proteins Bind to Sequences Adjacent to the SV40 Origin of Replication," *Cell,* 65:1083–1091 (Jun. 14, 1991).

J. Bargonetti et al., "Site–Specific Binding of Wild–Type p53 to Cellular DNA is Inhibited by SV40 T Antigen and Mutant p53," *Genes Dev.,* 6:1886–1898 (Oct. 1992).

L. Diller et al., "p53 Functions as a cell Cycle Control Protein in Osteosarcomas," *Mol. Cell. Biol.,* 10:5772–5781 (Nov. 1990).

S.J. Baker et al., "Suppression of Human Colorectal Carcinoma Cell Growth by Wild–type p53," *Science,* 249:912–915 (Aug. 24, 1990).

D. Eliyahu et al., "Wild–Type p53 can Inhibit Oncogene–Mediated Focus Formation," *Proc. Natl. Acad. Sci. USA,* 86:8763–8767 (Nov. 1989).

D. Eliyahu et al., "Participation of p53 Cellular Tumour Antigen in Transformation of Normal Embryonic Cells," *Nature,* 312:646–649 (Dec. 1984).

W.E. Mercer et al., "Negative Growth Regulation in a Glioblastoma Tumor Cell Line that Conditionally Expresses Human Wild–Type p53," *Proc. Natl. Acad. Sci. USA,* 87:6166–6170 (Aug. 1990).

C.A. Finlay et al., "The p53 Proto–Oncogene can Act as a Suppressor of Transformation," *Cell,* 57:1083–1093 (Jun. 30, 1989).

S. E. Kern et al., "Identification of p53 as a Sequence–Specific DNA–Binding Protein," *Science,* 252:1708–1711 (Jun. 21, 1991).

S.E. Kern et al., "Oncogenic Forms of p53 Inhibit p53–Regulated Gene Expression," *Science,* 256:827–830 (May 8, 1992).

J. Milner et al., "Cotranslation of Activated Mutant p53 with Wild Type Drives the Wild–Type p53 Protein into the Mutant Conformation," *Mol. Cell. Biol.,* 11:12–19 (Jan. 1991).

J. Milner and E.A. Medcalf, "Cotranslation of Activated Mutant p53 with Wild Type Drives the Wild–Type p53 Protein into the Mutant Conformation," *Cell,* 65:765–774 (May 31, 1991).

L.F. Parada et al., "Cooperation Between Gene Encoding p53 Tumour Antigen and ras in Cellular Transformation," *Nature,* 312:649–651 (Dec. 1984).

J.R. Jenkins et al., "Cellular Immortalization by a cDNA Clone Encoding the Transformation–Associated Phosphoprotein p53," *Nature,* 312:651–654 (Dec. 1984).

J. Martinez et al., "Cellular Localization and Cell Cycle Regulation by a Temperature–Sensitive p53 Protein," *Genes Dev.,* 5:151–159 (Feb. 1991).

T. Unger et al., "p53: A Transdominant Regulator of Transcription whose Function is Ablated by Mutations Occurring in Human Cancer," *EMBO J.,* 11:1383–1390 (Apr. 1992).

T. Unger et al., "Functional Domains of Wild–Type and Mutant p53 Proteins Involved in Transcriptional Regulation, Transdominant Inhibition, and Transformation Suppression," *Mol. Cell. Biol.,* 13:5186–5194 (Sep. 1993).

E. Shaulian et al., "Identification of a Minimal Transforming Domain of p53: Negative Dominance through Abrogation of Sequence–Specific DNA Binding," *Mol. Cell. Biol.,* 12:5581–5592 (Dec. 1992).

M. Reed et al., "p53 Domains: Suppression, Transformation, and Transactivation," *Gene Expression,* 3:95–107 (May 1993).

E. Yonish–Rouach et al., "Wild–type p53 Induces Apoptosis by Myeloid Leukemic Cells that is Inhibited by Interleukin–6," *Nature,* 352:345–347 (Jul. 25, 1991).

P. Shaw et al., "Induction of Apoptosis by wild–type p53 in Human Colon Tumor–Derived Cell Line," *Proc. Natl. Acad. Sci. USA,* 89:4495–4499 (May 1992).

T. Liu et al., "Growth Suppression of Human Head and Neck Cancer Cells by the Introduction of a Wild–Type p53 Gene via a Recombinant Adenovirus," *Cancer Res.,* 54:3662–3667 (Jul. 15, 1994).

Pellett et al., "Nucleotide Sequence and Predicted Amino Acid Sequence of a Protein Encoded in a Small Herpes Simplex Virus DNA Fragment Capable of Trans–Inducing alpha Genes," *Proc. Natl. Acad. Sci. USA,* 82:5870–5874 (Sep. 1985).

T. Fujiwara et al., "Induction of Chemosensitivity in Human Kung Cancer Cells in vivo by Adenovirus–Mediated Transfer of the Wild–Type p53 Gene," *Cancer Res.,* 54:2287–2291 (May 1, 1994).

T. Fujiwara et al., "A Retroviral Wild–Type p53 Expression Vector Penetrates Human Kung Cancer Spheroids and Inhibits Growth by Inducing Apoptosis," *Cancer Res.,* 53:4129–4133 (Sep. 15, 1993).

Bryson et al., "Protein Design: A Hierarchic Approach," *Science,* 270:935–940 (Nov. 1995).

Hupp et al., "Regulation of the Specific DNA Binding Function of p53," *Cell,* 71:875–886 (Nov. 1992).

Hollstein et al., "p53 Mutations in Human Cancers," *Science,* 253:49–53 (Jul. 5, 1991).

J.W. Sellers et al., "Changing Fos Oncoprotein to a Jun–independent DNA–binding Protein with GCN4 Dimerization Specificity by Swapping 'Leucine Zippers'," *Nature,* 341:74–75 (Sep. 7, 1989).

P. Oertel–Buchheit et al., "Spacing Requirements Between LexA Operator Half–Sites can be Relaxed by Fusing the LexA DNA Binding Domain with some Alternative Dimerization Domains," *J. Mol. Biol.,* 229(1):1–7 (Jan. 1993).

C.W. Miller et al., "Mutant p53 Proteins have Diverse Intracellular Abilities to Oligiomerize and Activate Transcription," *Oncogene,* 8(7):1815–1824 (Jul. 1993).

T.D. Halazonetis, "Wild–Type p53 Adopts a 'Mutant'–Like Conformation When Bound to DNA," *EMBO J.,* 12:1021–1028 (Mar. 1993).

T.D. Halazonetis, "An Enhancer <<Core>> DNA–Binding and Transcriptional Activity is Induced upon Transformation of Rat Embryo Fibroblasts," *Anticancer Res.,* 12:285–292 (Mar.–Apr. 1992).

T.D. Halazonetis and A.N. Kandil et al., "Conformational Shifts Propagate from the Oligiomerization Domain of p53 to its Tetrameric DNA Binding Domain and Restore DNA Binding to Select p53 Mutants," *EMBO J.,* 12:5057–5064 (Jan. 1993).

J. Waterman et al., "The Dihedral Symmetry of the p53 Tetramerization Domain Mandates a conformational Switch Upon DNA Binding," *EMBO J.,* 14:512–519 (Feb. 1, 1995).

K. Iwabuchi et al., "Use of the Two–hybrid System to Identify the Domain of p53 Involved in Oligiomerization," *Oncogene,* 8(6): 1693–1696 (Jun. 1993).

* cited by examiner

SEQUENCE LISTING

```
<160> NUMBER OF SEQ ID NOS: 4

<210> SEQ ID NO 1
<211> LENGTH: 1317
<212> TYPE: DNA
<213> ORGANISM: human p53
<220> FEATURE:
<221> NAME/KEY: CDS
<222> LOCATION: (136)..(1314)

<400> SEQUENCE: 1
gtctagagcc accgtccagg gagcaggtag ctgctgggct ccggggacac t ttgcgttcg      60 ggctgggagc gtgctttcca cgacggtgac acgcttccct ggattggcag c cagactgcc     120 ttccgggtca ctgcc atg gag gag ccg cag tca gat cct agc gtc gag ccc      171
                Met Glu Glu Pro Gln Ser Asp Pro Ser Val Glu Pro
                  1               5                  10 cct ctg agt cag gaa aca ttt tca gac cta t gg aaa cta ctt cct gaa      219
Pro Leu Ser Gln Glu Thr Phe Ser Asp Leu T rp Lys Leu Leu Pro Glu
             15                      20                  25 aac aac gtt ctg tcc ccc ttg ccg tcc caa g ca atg gat gat ttg atg      267
Asn Asn Val Leu Ser Pro Leu Pro Ser Gln A la Met Asp Asp Leu Met
         30                      35                  40 ctg tcc ccg gac gat att gaa caa tgg ttc a ct gaa gac cca ggt cca      315
Leu Ser Pro Asp Asp Ile Glu Gln Trp Phe T hr Glu Asp Pro Gly Pro
 45                      50                      55              60 gat gaa gct ccc aga atg cca gag gct gct c cc ccc gtg gcc cct gca      363
Asp Glu Ala Pro Arg Met Pro Glu Ala Ala P ro Pro Val Ala Pro Ala
                     65                      70                  75 cca gca gct cct aca ccg gcg gcc cct gca c ca gcc ccc tcc tgg ccc      411
Pro Ala Ala Pro Thr Pro Ala Ala Pro Ala P ro Ala Pro Ser Trp Pro
             80                      85                  90
```

```
ctg tca tct tct gtc cct tcc cag aaa acc t ac cag ggc agc tac ggt      459
Leu Ser Ser Ser Val Pro Ser Gln Lys Thr T yr Gln Gly Ser Tyr Gly
         95                 100                105 ttc cgt ctg ggc ttc ttg cat tct ggg aca g cc aag tct gta act tgc      507
Phe Arg Leu Gly Phe Leu His Ser Gly Thr A la Lys Ser Val Thr Cys
        110                 115                120 acg tac tcc cct gcc ctc aac aag atg ttt t gc caa ctg gcc aag acc      555
Thr Tyr Ser Pro Ala Leu Asn Lys Met Phe C ys Gln Leu Ala Lys Thr
125                 130                 135                140 tgc cct gtg cag ctg tgg gtt gat tcc aca c cc ccg ccc ggc acc cgc      603
Cys Pro Val Gln Leu Trp Val Asp Ser Thr P ro Pro Pro Gly Thr Arg
                145                 150                155 gtc cgc gcc atg gcc atc tac aag cag tca c ag cac atg acg gag gtt      651
Val Arg Ala Met Ala Ile Tyr Lys Gln Ser G ln His Met Thr Glu Val
                160                 165                170 gtg agg cgc tgc ccc cac cat gag cgc tgc t ca gat agc gat ggt ctg      699
Val Arg Arg Cys Pro His His Glu Arg Cys S er Asp Ser Asp Gly Leu
        175                 180                185 gcc cct cct cag cat ctt atc cga gtg gaa g ga aat ttg cgt gtg gag      747
Ala Pro Pro Gln His Leu Ile Arg Val Glu G ly Asn Leu Arg Val Glu
        190                 195                200 tat ttg gat gac aga aac act ttt cga cat a gt gtg gtg gtg ccc tat      795
Tyr Leu Asp Asp Arg Asn Thr Phe Arg His S er Val Val Val Pro Tyr
205                 210                 215                220 gag ccg cct gag gtt ggc tct gac tgt acc a cc atc cac tac aac tac      843
Glu Pro Pro Glu Val Gly Ser Asp Cys Thr T hr Ile His Tyr Asn Tyr
                225                 230                235 atg tgt aac agt tcc tgc atg ggc ggc atg a ac cgg aga ccc atc ctc      891
Met Cys Asn Ser Ser Cys Met Gly Gly Met A sn Arg Arg Pro Ile Leu
                240                 245                250 acc atc atc aca ctg gaa gac tcc agt ggt a at cta ctg gga cgg aac      939
Thr Ile Ile Thr Leu Glu Asp Ser Ser Gly A sn Leu Leu Gly Arg Asn
        255                 260                265 agc ttt gag gtg cgt gtt tgt gcc tgt cct g gg aga gac cgg cgc aca      987
Ser Phe Glu Val Arg Val Cys Ala Cys Pro G ly Arg Asp Arg Arg Thr
        270                 275                280 gag gaa gag aat ctc cgc aag aaa ggg gag c ct cac cac gag ctg ccc     1035
Glu Glu Glu Asn Leu Arg Lys Lys Gly Glu P ro His His Glu Leu Pro
285                 290                 295                300 cca ggg agc act aag cga gca ctg ccc aac a ac acc agc tcc tct ccc     1083
Pro Gly Ser Thr Lys Arg Ala Leu Pro Asn A sn Thr Ser Ser Ser Pro
                305                 310                315 cag cca aag aag aaa cca ctg gat gga gaa t at ttc acc ctt cag atc     1131
Gln Pro Lys Lys Lys Pro Leu Asp Gly Glu T yr Phe Thr Leu Gln Ile
                320                 325                330 cgt ggg cgt gag cgc ttc gag atg ttc cga g ag ctg aat gag gcc ttg     1179
Arg Gly Arg Glu Arg Phe Glu Met Phe Arg G lu Leu Asn Glu Ala Leu
        335                 340                345 gaa ctc aag gat gcc cag gct ggg aag gag c ca ggg ggg agc agg gct     1227
Glu Leu Lys Asp Ala Gln Ala Gly Lys Glu P ro Gly Gly Ser Arg Ala
350                 355                 360 cac tcc agc cac ctg aag tcc aaa aag ggt c ag tct acc tcc cgc cat     1275
His Ser Ser His Leu Lys Ser Lys Lys Gly G ln Ser Thr Ser Arg His
365                 370                 375                380 aaa aaa ctc atg ttc aag aca gaa ggg cct g ac tca gac tga            1317
Lys Lys Leu Met Phe Lys Thr Glu Gly Pro A sp Ser Asp
                385                 390
```

-continued

```
<210> SEQ ID NO 2
<211> LENGTH: 393
<212> TYPE: PRT
<213> ORGANISM: human p53

<400> SEQUENCE: 2

Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365
```

-continued

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 3
<211> LENGTH: 393
<212> TYPE: PRT
<213> ORGANISM: human p53

<400> SEQUENCE: 3

Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Phe Gln Ile Arg Gly Arg Glu
                325                 330                 335

Arg Phe Glu Phe Phe Arg Glu Leu Asn Glu Ile Met Glu Leu Lys Asp
            340                 345                 350

```
Leu Leu Asp Gly Lys Glu Pro Gly Gly Ser Arg Ala His Ser Ser His
        355                 360                 365
Leu Lys Ser Lys Lys Gly Gln Ser Thr Ser Arg His Lys Lys Leu Met
        370                 375                 380
Phe Lys Thr Glu Gly Pro Asp Ser Asp
385                 390

<210> SEQ ID NO 4
<211> LENGTH: 393
<212> TYPE: PRT
<213> ORGANISM: human p53

<400> SEQUENCE: 4

Met Glu Glu Pro Gln Ser Asp Pro Ser Val Glu Pro Pro Leu Ser Gln
  1               5                  10                  15
Glu Thr Phe Ser Asp Leu Trp Lys Leu Leu Pro Glu Asn Asn Val Leu
             20                  25                  30
Ser Pro Leu Pro Ser Gln Ala Met Asp Asp Leu Met Leu Ser Pro Asp
         35                  40                  45
Asp Ile Glu Gln Trp Phe Thr Glu Asp Pro Gly Pro Asp Glu Ala Pro
     50                  55                  60
Arg Met Pro Glu Ala Ala Pro Pro Val Ala Pro Ala Pro Ala Ala Pro
 65                  70                  75                  80
Thr Pro Ala Ala Pro Ala Pro Ala Pro Ser Trp Pro Leu Ser Ser Ser
                 85                  90                  95
Val Pro Ser Gln Lys Thr Tyr Gln Gly Ser Tyr Gly Phe Arg Leu Gly
                100                 105                 110
Phe Leu His Ser Gly Thr Ala Lys Ser Val Thr Cys Thr Tyr Ser Pro
            115                 120                 125
Ala Leu Asn Lys Met Phe Cys Gln Leu Ala Lys Thr Cys Pro Val Gln
        130                 135                 140
Leu Trp Val Asp Ser Thr Pro Pro Gly Thr Arg Val Arg Ala Met
145                 150                 155                 160
Ala Ile Tyr Lys Gln Ser Gln His Met Thr Glu Val Val Arg Arg Cys
                165                 170                 175
Pro His His Glu Arg Cys Ser Asp Ser Asp Gly Leu Ala Pro Pro Gln
            180                 185                 190
His Leu Ile Arg Val Glu Gly Asn Leu Arg Val Glu Tyr Leu Asp Asp
        195                 200                 205
Arg Asn Thr Phe Arg His Ser Val Val Pro Tyr Glu Pro Pro Glu
    210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
                245                 250                 255
Leu Glu Asp Ser Ser Gly Asn Leu Leu Gly Arg Asn Ser Phe Glu Val
            260                 265                 270
Arg Val Cys Ala Cys Pro Gly Arg Asp Arg Arg Thr Glu Glu Glu Asn
        275                 280                 285
Leu Arg Lys Lys Gly Glu Pro His His Glu Leu Pro Pro Gly Ser Thr
    290                 295                 300
Lys Arg Ala Leu Pro Asn Asn Thr Ser Ser Ser Pro Gln Pro Lys Lys
305                 310                 315                 320
Lys Pro Leu Asp Gly Glu Tyr Phe Thr Phe Gln Ile Arg Gly Arg Glu
                325                 330                 335
```

```
-continued

Arg Phe Glu Met Phe Arg Glu Leu Asn Glu Ile Met Glu Leu Lys Asp
            340                 345                 350

Leu Leu Asp Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

MODIFIED P53 TETRAMERIZATION DOMAINS HAVING HYDROPHOBIC AMINO ACID SUBSTITUTIONS

CROSS REFERENCE TO RELATED APPLICATIONS

This application claims priority of US Provisional Patent Application No. 60/084,839, filed May 8, 1998.

FIELD OF THE INVENTION

The present invention relates generally to p53 and its use in treatment of conditions associated with inappropriate levels of p53 tumor suppressor activity.

BACKGROUND OF THE INVENTION

Wild-type p53 is a sequence-specific transcription factor that induces cell cycle arrest or programmed cell death in response to DNA damage [W. Maltzman and L. Czyzyk, Mol. Cell. Biol., 4:1689–1694 (1984); M. B. Kastan et al., Cancer Res., 51: 6304–6311 (1991); S. W. Lowe, et. al., Cell, 74: 957–967 (1993); S. W. Lowe, et. al., Nature, 362: 847–849 (1993); A. R. Clarke, et. al., Nature. 362: 849–852 (1993); A. D. Leonardo, et. al., Genes Dev., 8: 2540–2551 (1994)]. The N-terminus of p53 contains a transactivation domain [S. Fields and S. K. Jang, Science 249: 1046–1049 (1990); T. Unger et al., EMBO J. 11: 1383–1390 (1992)], the central region a sequence-specific DNA binding domain [J. Bargonetti, et. al., Genes Dev., 7: 2565–2574 (1993); N. P. Pavletich, et. al., Genes Dev, 7: 2556–2564 (1993); Y. Wang et. al., Genes Dev, 7: 2575–2586 (1993); T. D. Halazonetis and A. N. Kandil, et. al., EMBO J. 12: 5057–5064 (1993)], and the C-terminus a tetramerization domain [J. Milner, et. al., Mol. Cell. Biol. 11: 12–19 (1991); H. W. Stürzbecher, et. al., Oncogene, 7: 1513–1523 (1992); H. Sakamoto, et. al., Proc. Natl. Acad. Sci. U.S.A. 91: 8974 (1994); P. Wang, et. al, Mol. Cell. Biol. 14: 5182–5191 (1994)]. The tetramerization domain mediates homo-oligomerization, which is required for high affinity sequence-specific DNA binding activity and tumor suppressor function [Pietenpol et. al., Proc. Natl. Acad. Sci. USA, 91:1998–2002 (1994)].

In about half of all human tumors, the sequence-specific DNA binding domain of p53 is inactivated by point mutations [C. C. Harris, Science, 262: 1980–1981 (1993); S. Friend, Science, 265: 334–335 (1994); J. Bargonetti, et. al., Cell, 65: 1083–1091 (1991); S. E. Kern et. al., Science 252: 1708–1711 (1991)]. The tumor-derived p53 mutants fail to suppress tumor growth [L. Diller, et. al., Mol. Cell. Biol., 10: 5772–5781 (1990); S. J. Baker, et. al., Science, 249: 912–915 (1990); D. Eliyahu, et. al, Proc. Natl. Acad. Sci., USA, 86: 8763–8767 (1989); W. E. Mercer, et. al., Proc. Natl. Acad. Sci. USA, 87: 6166–6170 (1990); C. A. Finlay, et. al., Cell, 57: 1083–1093 (1989)] and also transdominantly inhibit wild-type p53 [J. Martinez, et. al., Genes Dev., 5: 151–159 (1991); J. Bargonetti, et. al, Genes Dev., 6: 1886–1898, (1992); S. E. Kern, et. al., Science, 256: 827–830 (1992); J. Miner and E. A. Medcalf, Cell, 65: 765–774 (1991); D. Eliyahu, et. al, Nature 312: 646–649 (1984); L. F. Parada, et. al., Nature 312: 649–651 (1984); J. R. Jenkins, et. al., Nature 312: 651–654 (1984)]. There is significant evidence that transdominant inhibition of wild-type p53 is mediated by sequestration of wild-type p53 into inactive mutant/wild-type heterotetramers. The ability of tumor-derived p53 mutants to transdominantly inhibit wild-type p53 requires an intact tetramerization domain. The isolated p53 tetramerization domain also inhibits wild-type p53 function [T. Unger, et. al., Mol. Cell. Biol., 13: 5186–5194 (1993); E. Shaulian, et. al., Mol. Cell. Biol., 12: 5581–5592 (1992); M. Reed, et. al., Gene Expression 3: 95–107 (1993)]. Chimeric p53 proteins that contain a heterologous tetramerization domain, instead of the native p53 tetramerization domain, are not transdominantly inhibited by tumor-derived p53 mutants.

Induction of wild-type p53 function in tumor cells leads to growth arrest or apoptosis (L. Diller, cited above; S. J. Baker, cited above; W. E. Mercer, cited above; E. Yonish-Rouach, et. al., Nature, 352: 345–347 (1991); P. Shaw, et. al., Proc. Natl. Acad. Sci. USA, 89: 4495–4499 (1992)]. Thus, introduction of wild-type p53 into tumor cells could in principle be utilized for therapy [T. Fujiwara, et. al., Cancer Res., 53: 4129–4133 (1993); T. Fujiwara, et. al., Cancer Res., 54: 2287–2291 (1994); T. Liu, et. al., Cancer Res., 54: 3662–3667 (1994). One obstacle to the effectiveness of such therapy, however, is that about half of all human tumors express dominant negative p53 mutants [Harris et al, cited above, S. Friend et al, cited above, J. Bargonetti et al, cited above; S. E. Kern et. al., cited above.].

The design and analysis of a p53 chimeric protein in which the native p53 oligomerization domain is substituted with a modified leucine zipper that assembles as a tetramer has been reported [See, e.g., U. S. Pat. No. 5,573,925]. This engineered p53 protein is not transdominantly inhibited by tumor-derived p53 mutants, but is not as active as wild-type p53.

What are needed are constructs and methods for providing p53 tumor suppressor activity, particularly in the presence of insufficient activity due to the presence of tumor-derived p53 mutants or other factors.

SUMMARY OF THE INVENTION

In a first aspect, the present invention provides a modified p53 protein containing a p53 DNA binding domain and a modified p53 tetramerization domain that does not hetero-oligomerize with the native p53 tetramerization domain. The modified tetramerization contains the sequence of amino acid residues 325 to 355 of a human p53 or a homologous p53 sequence which has been modified at one or more of the following residues (with reference to the numbering scheme of the human p53 in SEQ ID NO: 2): Leu330 substituted with Phe; Met340 substituted with Phe; Ala347 substituted with Ile; Leu348 substituted with Met; Ala353 substituted with Leu; Gln354 substituted with Leu; and/or Ala355 substituted with Asp.

In another aspect, the present invention provides a pharmaceutical composition comprising a pharmaceutically acceptable carrier; and a modified p53 protein of the invention.

In still another aspect, the present invention provides a nucleic acid molecule encoding a modified p53 protein of the invention. Optionally, this molecule may further contain regulatory sequences which direct expression of said modified tetramerization domain or modified p53 protein.

In yet another aspect, the present invention provides a vector containing a nucleic acid sequence of the invention and sequences which direct expression thereof In still a further aspect, the present invention provides a pharmaceutical composition comprising a nucleic acid sequence of the invention and a pharmaceutically acceptable carrier.

In yet a further aspect, the present invention provides a method of treating a condition associated with abnormal p53 activity comprising the step of administering a pharmaceutical composition as described above.

DETAILED DESCRIPTION OF THE INVENTION

The present invention provides modified p53 proteins containing modified tetramerization domains having altered oligomerization specificity. The modified p53 proteins of the invention form homo-tetramers and have tumor suppressor function, but do not hetero-oligomerize with tumor-derived p53 mutants and resist transdominant inhibition.

The modified tetramerization domains of the invention contain at least one of the following substitutions within the hydrophobic core of the p53 tetramerization domain, which is located in the region of about amino acids 325 to about 355, with reference to human p53: Leu330 substituted with Phe; Met340 substituted with Phe; Ala347 substituted with Ile; Leu348 substituted with Met; Ala353 substituted with Leu; Gln354 substituted with Leu and/or Ala355 substituted with Asp. In a currently preferred embodiment, a modified p53 protein construct of the invention contains a modified human p53 tetramerization domain, with all seven of the amino acid substitutions identified herein.

The present inventors have found that the modified p53 tetramerization domains, when engineered into modified p53 protein constructs block the interaction of wild-type p53 with tumor-derived p53 mutants. The modified p53 tetramerization domains of the invention contain amino acid substitutions within the p53 tetramerization domain that change oligomerization specificity. The p53 tetramerization domains modified in this way still forms tetramers, but do not hetero-oligomerize with the unmodified (native) domain. The inventors have found that, unlike the prior art constructs which utilized leucine zippers which cause oligomerization specificity to be determined primarily by charged residues, conservative hydrophobic amino acid substitutions change the oligomerization specificity of the p53 tetramerization domain.

All references to human p53 residue numbers herein refer to the numbering scheme provided by Zakut-Houri et al, (1985) *EMBO J.*, 4: 1251–1255 (1985) [GenBank Code Hsp53], which is incorporated by reference, and reproduced in SEQ ID NOS: 1 and 2However, one of skill in the art will readily understand that the sequences referenced herein may be obtained by a variety of known techniques including, e.g., chemical synthesis. Additionally, where reference is made to the human p53 residue numbers, one of skill in the art will readily understand that corresponding sequences from homologous p53 sequences may be readily substituted. For example, the corresponding sequences (e.g., to amino acid residues 325 to 355 of human p53, SEQ ID NO: 2) may be readily determined by reference to the alignment of the human sequences to a variety of non-human p53 sequences provided in Soussi et al, *Oncogene*, 5: 945–952 (1990), cited above. The alignment of additional p53 sequences homologous to human p53 may be obtained by commercially available computer programs, such as BESTFIT of the University of Wisconsin GCG package. The homolog of p53 which can be used to substitute for the human p53 sequences can be readily selected by one of skill in the art.

Desirably, these modified tetramerization domains are contained within a protein construct which further contains a p53 DNA binding domain.

I. P53 Protein Constructs

The present invention provides a modified p53 protein construct which contains a p53 DNA binding domain and a modified tetramerization domain, as described herein. These p53 protein constructs may contain sequences from a single source or from multiple sources, e.g., these constructs may contain sequences which were chemically synthesized, sequences which were derived from a human p53, sequences which were derived from a non-human p53, or combinations thereof.

As defined herein, chimeric p53 protein constructs of the invention include proteins containing an N-terminal portion of p53 containing at least a DNA binding domain fused, optionally via a suitable linker, to the modified p53 tetramerization domain described herein. When utilized, linkers may be readily selected from among those known to those of skill in the art. While these linkers may be chemical compounds or other inorganic constructs, they are more desirably amino acids or peptides. Regardless of the type of linker used, the linkers do not interfere with the function of the p53 chimeric protein. See, U.S. Pat. No. 5,573,925 for examples of suitable linkers.

The ability of p53 to bind DNA in a sequence-specific manner maps to about amino acid 93 to about amino acid 293 of human p53, SEQ ID NO: 2 [Halazonetis and Kandil, *EMBO J.*, 12: 5057–5064 (1993); Pavletich et al, *Genes Dev.*, 7: 2556–2564 (1993); Wang et al, *Genes Dev.*, 7: 2575–2586 (1993)]. Thus, this region is a particularly suitable DNA binding domain. However, modifications to this region which do not substantially reduce the p53 DNA binding ability and/or specificity may be incorporated into the p53 protein constructs of the invention. Such modifications include naturally occurring or engineered mutants. For example, suitable mutants include, without limitation, p53 having glutamine at residue 248 (p53Q248), p53 having histidine at residue 273 (p53H273), and p53 having cysteine at residue 273 (p53C273). Other p53 mutants include those having a mutation of the native Thr284 to Arg or Lys, as described in WO 97/10843.

The p53 constructs of the invention may further contain native p53 N-terminal (i.e., residues about 1 to about 93 of human p53, SEQ ID NO: 2) and C-terminal residues (i.e., residues about 256 to about 393 of human p53, SEQ ID NO: 2). Alternatively, the p53 constructs of the invention may contain deletions or modification in either of the N-terminus or C-terminus, as desired. One particularly desirable N-terminal deletion involves substitution of the p53 transaction domain (e.g., about aa 3 to about aa 80 of human p53, SEQ ID NO: 2) with the transactivation domain derived from another protein (e.g., the herpes simplex virus protein VP16 domain, aa residues 402–479 of VP16, described in Pellett et al, Proc. Natl. Acad. Sci. USA, 82:5870–5874 (1985); GenBank Code He11cg]. One particularly desirable C-terminal deletion involves truncation of about amino acid 364 to about amino acid 393 of human p53, SEQ ID NO: 2However, suitable deletions include truncation following amino acid residue 355, and deletions internal to the region corresponding to residues 356–393 of human p53, SEQ ID NO: 2.

A currently preferred modified p53 protein construct of the invention, which contains full-length p53 modified to contain a p53 tetramerization domain of the invention, is termed herein p53IND7 [SEQ ID NO: 3]. P53IND7 has very similar properties to the wild-type tetramerization domain. Both domains assemble as tetramers and support the sequence-specific DNA binding, transactivation and tumor suppressor functions of p53Furthermore, p53IND7 is anticipated to have a three-dimensional structure that is very similar to the structure of the wild-type domain. In fact, because six of the seven substitutions involve buried residues, the surfaces of the p53wt [SEQ ID NO: 2] and p53IND7 [SEQ ID NO: 3] domains may be remarkably similar.

The high functional and structural similarity between the p53IND7 [SEQ ID NO: 3] and p53wt [SEQ ID NO: 2] domains, suggests that p53IND7 can be used to study p53 function in cells containing high levels of endogenous wild-type or mutant p53More significantly, p53IND7 could be used in a gene therapy approach for treatment of human cancer [T. Fujiwara et al., *Cancer Res.*, 53:4129–4133 (1993); T. Figiwara et al, *Cancer Res.*, 54:2287–2291 (1994); T. J. Liu et al, *Cancer Res.*, 54:3662–3667 (1994)]. A p53 protein with altered oligomerization specificity would be clearly superior to wild-type p53 for such therapy, since about half of all human tumors express p53 mutants that can inhibit wild-type p53 activity [C. C. Harris, cited above; S. Friend, cited above].

The modifications described herein may be engineered using known techniques, e.g., by chemical synthesis techniques or by mutating the nucleic acid sequences encoding the amino acid which is to be altered using conventional site-directed mutagenesis techniques [R. Higuchi et al, in M. A. Innis et al, (eds.), *PCR Protocols: A Guide to Methods and Applications*, Academic Press, San Diego, pp. 177–183 (1990)].

II. Nucleic Acid Sequences Encoding Modified p53 Proteins of the Invention

The present invention further provides nucleic acid sequences encoding the modified p53 proteins and tetramerization domains of this invention. In addition to the coding strand, the nucleic acid sequences of the invention include the complementary DNA sequence representing the non-coding strand, the messenger RNA sequence, the corresponding cDNA sequence and the RNA sequence complementary to the messenger RNA sequence. Variants of these nucleic acids of the invention include variations due to the degeneracy of the genetic code and are encompassed by this invention. Such variants may be readily identified and/or constructed by one of skill in the art. In certain cases specific codon usage may be employed to optimize expression. The above nucleotide sequences can be included within larger DNA or RNA fragments, or may be interrupted by introns.

A. Expression Vectors

In another embodiment, the nucleic acids encoding the proteins of the invention are present in the context of vectors suitable for amplification in prokaryotic or eukaryotic cells. Many such vectors are known and many of these are commercially available. For example plasmids with bacterial or yeast replication origins allow amplification in bacteria or yeast, respectively. Such vectors allow the production of large quantities of nucleic acids encoding the proteins of the invention, which nucleic acids can be used for gene therapy or for expression of the modified p53 proteins of the invention.

In yet another embodiment the nucleic acids encoding the proteins of the invention are present in the context of vectors suitable for expression in cell-free extracts or lysates or in prokaryotic or eukaryotic cells. Many such vectors are known [Ausubel et al, *Current Protocols in Molecular Biology*, Greene Publishing Associates and John Wiley & Sons, N.Y. (1997)] and many of these are commercially available. For example, the vector pGEM4 (Promega, Madison, Wis.) is suitable for expression of the proteins in cell-free lysates, while the vector pSV2 [ATCC] is suitable for expression in mammalian cells. Such vectors allow the production of the proteins of the invention in vitro for analysis of their functional properties or for delivery to patients either directly or indirectly (i.e., ex vivo).

B. Gene Therapy Vectors

The nucleic acid sequences of the invention may be inserted into a vector capable of targeting and infecting a desired cell, either in vivo or ex vivo for gene therapy, and causing the encoded modified protein of this invention to be expressed by that cell. Many such viral vectors are useful for this purpose, e.g., adenoviruses, retroviruses and adeno-associated viruses (AAV) [Schreiber et al., *Biotechniques*, 14: 818–823 (1993); Davidson et al., *Nature Genetics*, 3: 219–223 (1993); Roessler et al., *J. Clin. Invest.*, 92: 1085–1092 (1993); Smythe et al., *Ann. Thorac. Surg.*, 57: 1395–1401 (1994); Kaplitt et al, *Nature Genetics*, 8: 148–154 (1994)]. There has already been success using viral vectors driving expression of wild-type p53 [Fujiwara et al., *Cancer Res.*, 53: 4129–4133 (1993); Fujiwara et al., *Cancer Res.*, 54: 2287–2291 (1994); Friedmann, *Cancer*, 70(6 Suppl): 1810–1817 (1992); Fujiwara et al., *Curr. Opin. Oncol.*, 6: 96–105 (1994b); Roth et al., *Nature Medicine*, 2:985–991 (1996)].

For use in gene therapy, these viral vectors containing nucleic acid sequences encoding a protein of the invention, e.g., a modified p53 protein, are prepared by one of skill in the art with resort to conventional techniques (see references mentioned above). For example, a recombinant viral vector, e.g. an adenovirus, of the present invention comprises DNA of at least that portion of the viral genome which is capable of infecting the target cells operatively linked to the nucleic acid sequences of the invention. By "infection" is generally meant the process by which a virus transfers genetic material to its host or target cell. Preferably, the virus used in the construction of a vector of the invention is rendered replication-defective to remove the effects of viral replication on the target cells. In such cases, the replication-defective viral genome can be packaged by a helper virus in association with conventional techniques.

Briefly, the vector(s) containing the nucleic acids encoding an altered protein of the invention is suspended in a pharmaceutically acceptable carrier, such as saline, and administered parenterally (or by other suitable means) in sufficient amounts to infect the desired cells and provide sufficient levels of modified protein to achieve the desired therapeutic or prophylactic effect, e.g., sufficient p53 activity to arrest abnormal cellular proliferation. Other pharmaceutically acceptable carriers are well known to those of skill in the art. A suitable amount of the vector containing the chimeric nucleic acid sequences is between about $10^6$ to $10^9$ infectious particles per mL carrier. The delivery of the vector may be repeated as needed to sustain satisfactory levels of biological activity. For example, where modified p53 is administered, activity may be determined by monitoring clinical symptoms.

As desired, this therapy may be combined with other therapies for the disease or condition being treated. For example, therapy involving the administration of a vector capable of expressing a modified p53 protein of the invention is well suited for use in conjunction with conventional cancer therapies, including surgery, radiation and chemotherapy.

Nucleic acid sequences driving expression of a protein of the invention may also be introduced by "carriers" other than viral vectors, such as liposomes, nucleic acid-coated gold beads or can simply be injected in situ [Fujiwara et al (1994b), cited above; Fynan et al., *Proc. Natl. Acad. Sci. USA*, 90: 11478–11482 (1993); Cohen, *Science*, 259: 1691–1692 (1993); Wolffet a., *Biotechnigues*, II: 474–485 (1991)].

III. Pharmaceutical Compositions

The altered proteins and nucleic acid sequences of this invention may also be formulated into pharmaceutical compositions and administered using a therapeutic regimen compatible with the particular formulation. When administered in the form of nucleic acid sequences, the composition may contain "naked" DNA, or a plasmid containing the nucleic acid sequences which may contain the regulatory elements necessary to drive expression of the modified p53 proteins of the invention. As used herein, the term "naked DNA" means substantially pure DNA which is not associated with a protein, lipid, carbohydrate or contained within a cell or an artificial delivery system such as a liposome.

Pharmaceutical compositions within the scope of the present invention include compositions containing a modified protein of the invention (or a nucleic acid sequence encoding a modified protein) in an effective amount to have the desired physiological effect, e.g. to arrest the growth of cancer cells without causing unacceptable toxicity for the patient.

Suitable formulations for parenteral administration include aqueous solutions of the active compounds in water-soluble or water-dispersible form, e.g. saline. Alternatively, suspensions of the active compounds may be administered in suitable conventional lipophilic carriers or in liposomes.

The compositions may be supplemented by active pharmaceutical ingredients, where desired. Optional antibacterial, antiseptic, and antioxidant agents in the compositions can perform their ordinary functions. The pharmaceutical compositions of the invention may further contain any of a number of suitable viscosity enhancers, stabilizers, excipients and auxiliaries which facilitate processing of the active compounds into preparations that can be used pharmaceutically. Preferably, these preparations, as well as those preparations discussed below, are designed for parenteral administration. However, compositions designed for oral or rectal administration are also considered to fall within the scope of the present invention.

Those of skill in the pharmaceutical art should be able to derive suitable dosages and schedules of administration. As used herein, the terms "suitable amount" or "effective amount" means an amount which is effective to treat the conditions referred to below. A preferred dose of a pharmaceutical composition containing a protein of this invention is generally effective above about 0.1 mg modified protein per kg of body weight (mg/kg), and preferably from about 1 mg/kg to about 100 mg/kg. These doses may be administered with a frequency necessary to achieve and maintain satisfactory activity levels. Although a preferred range has been described above, determination of the effective amounts for treatment of each type of tumor or other condition may be determined by those of skill in the art.

Dosage units of such pharmaceutical compositions containing the proteins of this invention preferably contain about 1 mg to 5 g of the protein.

IV. Therapeutic Indications

The nucleic acids encoding modified p53 proteins and the modified p53 proteins themselves can be introduced into human patients for therapeutic benefits in conditions characterized by insufficient wild-type p53 activity. Such conditions have been described in the art. See, e.g., PCT/US95/15353 (Jun. 6, 1996). For example, the pharmaceutical compositions of the invention, including the gene therapy vectors, may be employed to induce the cellular defense to DNA damaging agents such as sunlight UV irradiation, as well as radiation and chemotherapeutics used for cancer treatment. The therapeutic indications include inducing apoptosis of specific cells, such as proliferating lymphocytes, the prevention of transplant rejection, and the treatment of autoimmune diseases, e.g., systemic lupus erythrematosis, rheumatoid arthritis and the like.

The pharmaceutical compositions of this invention may also be employed to restore p53 function in tumor cells and to suppress cell proliferation in diseases other than cancers, which are characterized by aberrant cell proliferation. Among such diseases are included psoriasis, atherosclerosis and arterial restenosis. A variety of other suitable indications which will be readily apparent to one of skill in the art.

V. Antibodies

The modified p53 tetramerization domains and modified p53 protein constructs of the invention are useful for generating antibodies, which may be used as diagnostic reagents, for example, to monitor the presence of modified protein or modified tetramerization domain.

Specific antisera may be generated using known techniques. See, Sambrook, cited above, Chapter 18, generally, incorporated by reference. Similarly, antibodies of the invention, both polyclonal and monoclonal, may be produced by conventional methods, including the Kohler and Milstein hybridoma technique, recombinant techniques, such as described by Huse et al, *Science*, 246:1275–1281 (1988), or any other techniques known to the art.

The invention further encompasses functional fragments of the antibodies of the invention, including, Fab, $F_v$, and $F(ab')_2$ fragments, the binding site of the antibodies, and the complementarity determining regions (CDRs). Optionally, the binding site and/or CDRs may be contained in a synthetic molecule which provides antibody framework regions. Further, these functional fragments may be used in the production of recombinant antibodies, including bifunctional antibodies, chimeric antibodies, and humanized antibodies, which preferably retain the antigen binding specificity of the antibodies of the invention. Such recombinant antibodies may be constructed and produced according to known techniques [see, e.g., S. D. Gillies et al, *J. Immunol. Meth.*, 125:191–202 (1989); and G. E. Mark and E. A. Pladlan, "Humanization of Monoclonal Antibodies", *The Handbook of Experimental Pharmacology*, Vol. 113, Chapter 4, pp. 105–133, Springer-Verlag (June, 1994)]. These functional fragments and recombinant antibodies may be used for a variety of purposes, including any of those described herein for the antibodies of the invention.

In general, polyclonal antisera, monoclonal antibodies and other antibodies which bind to an altered protein as antigen are useful as research tools, as diagnostic reagents, as therapeutic agents, and for producing other antibodies (as described above) which are similarly useful.

VI. Diagnostic Reagents

The modified p53 proteins of the invention may be used as diagnostic reagents. These reagents may optionally be labeled using diagnostic labels, such as radioactive labels, colorimetric enzyme label systems and the like conventionally used in diagnostic or therapeutic methods. Alternatively, the—or C-terminus of a modified p53 protein of the invention may be tagged with a detectable label which can be recognized by a specific antisera. For example, the reagents derived from p53 may be used in diagnosis of a variety of conditions associated with p53 and/or aberrant cell proliferation, including autoimmune diseases, e.g., systemic lupus erythrematosis, rheumatoid arthritis and the like, cancers, psoriasis, atherosclerosis and arterial restenosis. For example, in tissue biopsies, the presence of p53 could be directly verified by RT-PCR or immunostaining. Reagents produced from other altered proteins of the invention, e.g., antibodies and the like, may similarly be utilized as diagnostic reagents. The selection of the appropriate assay format and label system is within the skill of the art and may readily be chosen without requiring additional explanation by resort to the wealth of art in the diagnostic area.

These examples illustrate the method of the invention as performed in connection with p53 and the preparation of modified p53 proteins of the invention. These examples are illustrative only and do not limit the scope of the invention.

These examples illustrate the preferred method for preparing exemplary modified p53 constructs of the invention and the biological activity of the modified p53 constructs. These examples are illustrative only and do not limit the scope of the invention.

EXAMPLE 1

Recombinant Plasmids

Standard cloning procedures were used [F. M. Ausubel et al, Current Protocols in Molecular Biology, New York:Green/Wiley Publishing Associates (1994)]. Plasmids of the pGEM series were used to generate in vitro translated p53 proteins [T. D. Halazonetis and A. N. Kandil, *EMBO J.*, 12:5057–5064 (1993); T. D. Halazonetis et al, *EMBO J.*, 12:1021–1028 (1993); J. Waterman et al, *EMBO J.*, 14:512–519 (1995)].

pGEMhp53IND plasmids were derived from pGEMhp53wtB by PCR-directed mutagenesis and used to express in vitro-translated full-length p53 proteins with modified tetramerization domains. Plasmids pSV2hp53IND6 [encoding SEQ ID NO: 4] and pSV2hp53IND7 [encoding SEQ ID NO: 3] were derived from pSV2hp53wtB by substituting the Sst I-Sal I fragment that encodes the wild-type p53 tetramerization domain with the corresponding fragments of the pGEMhp53IND plasmids. Plasmid pT5Thp53IND7 is derived from pT5Thp53wt and is used to express the modified p53 tetramerization domain in *E. coli*.

Plasmids pEp21/TKseap and pEmdm2/TKseap are reporter plasmids containing p53 response elements [T. Halazonetis, *Anticancer Res.*, 12:285–292 (1992)].

For analysis of DNA binding activity the p53 proteins were incubated with $^{32}$P-labeled oligonucleotides and subjected to electrophoresis [Halazonetis and Kandil, cited above; Halazonetis, cited above; Waterman, cited above]. Oligonucleotides BC, BC.V4A.S10 [Waterman et al, cited above], Ep21 and Emdm2 each contain a p53 binding site, while oligonucleotide TF3 is a non-specific DNA [Halazonetis, *EMBO J.*, 12:1021–1028 (1993)].

EXAMPLE 2

Repacking the p53 Tetramerization Domain Hydrophobic Core

The three-dimensional structure of the p53 tetramerization domain has been determined by X-ray crystallography and NMR spectroscopy [G. M. Clore et al., *Science*, 265: 386 (1994); W. Lee et al., *Nature Structural Biol.*, 1: 877 (1994); G. M. Clore et al., *Nature Structural Biol.*, 2: 321 (1995); P. D. Jeffrey et al., *Science*, 267: 1498 (1995)]. The domain has a well-defined globular hydrophobic core, and contains both β-sheet and α-helical secondary structure elements. The four identical subunits are arranged as a dimer of dimers; in the primary dimer the β-strands pack antiparallel, as do the α-helices (the two subunits whose β-strands form an antiparallel β-sheet are referred to herein as the primary dimer, because of the large subunit surface area that is buried in this intersubunit interface). Across primary dimers, the α-helices pack parallel at an 81° angle. See, FIG. 1 of M. McCoy et al, *EMBO J*, 16(290): 6230–6236 (1997).

The well-packed hydrophobic core of the p53 tetramerization domain can be divided in three compartments: the part of the core that mediates interactions exclusively within the primary dimers; the part of the core that mediates interactions exclusively across primary dimers and the central part of the core that mediates interactions both within and across primary dimers [McCoy, cited above]. To change the oligomerization specificity of the domain, we targeted residues mediating interactions both within and across primary dimers.

We initially probed for amino acid substitutions that compromise oligomerization on the rationale that such substitutions would identify residues that make critical intersubunit contacts. Oligomerization would be examined in the context of a full-length human p53 protein using a sequence-specific DNA binding assay, which allows many mutants to be analysed rapidly. With this assay, oligomerization is measured indirectly, because monomeric full-length p53 does not bind DNA. We initiated the mutagenesis by targeting Leu330, whose α-carbon maps to the center of the β-strands and whose side chain is involved in hydrophobic interactions between the two subunits that form the primary dimer.

Substitution of Leu330 with Phe had no effect on the sequence-specific DNA binding activity of p53. Residues Ala347 and Leu348, which map towards the C-termini of the α-helices and whose side chains are involved primarily in hydrophobic interactions across primary dimers, were subsequently substituted with Ile and Met, respectively. This double substitution also did not affect DNA binding. However, the triple substitution of Leu330, Ala347 and Leu348 with Phe, Ile and Met, respectively, abolished sequence-specific DNA binding suggesting loss of oligomerization.

We rationalized that the triple substitution abrogated oligomerization by disrupting the hydrophobic interactions that stabilize the three-dimensional structure of the native domain. According to this hypothesis, introducing novel hydrophobic interactions might restore oligomerization and lead to an engineered domain that can no longer oligomerize with the native domain due to the distinct architecture of stabilizing hydrophobic interactions.

We first attempted to introduce novel hydrophobic interactions across the primary subunits. The three C-terminal residues of the α-helix, Ala353, Gln354 and Ala355, were substituted with Leu, Leu and Asp, respectively. Remarkably, these substitutions restored sequence-specific DNA binding activity to the Phe330-Ile347-Met348 triple mutant, although not to wild-type p53 levels. To introduce additional hydrophobic interactions, Met340 at the interface of all four subunits was substituted with Phe in an effort to further enhance the hydrophobic interactions both within and across primary dimers. This substitution together with the three substitutions at the C-termini of the α-helices, restored the sequence-specific DNA binding activity of the Phe330-Ile347-Met348 triple mutant to essentially wild-type levels. This implies that the modified tetramerization domain allows p53 to oligomerize with high efficiency, because oligomerization is required for sequence-specific DNA binding. Furthermore, the modified p53 protein must assemble as a tetramer, because in complex with DNA it comigrates with wild-type p53 tetramers; oligomers other than tetramers do not comigrate with tetramers in this assay. The engineered p53 tetramerization domain with the seven amino acid substitutions, is hereafter referred to as IND (independent tetramerization domain), because as demonstrated below it does not interact with wild-type p53 or tumor-derived p53 mutants.

Seven amino acid substitutions distinguish p53wt and p53IND7Understanding how these substitutions change oligomerization specificity requires high resolution structural information for p53wt and p53IND7. Such information is only available for p53wt. The change in oligomerization specificity can be considered to involve two steps. In the first step, the substitutions targeting Leu330, Ala347 and Leu348 disrupt oligomerization. In the second step, the substitutions targeting Met340, Ala353, Gln354 and Ala355 restore oligomerization resulting in a domain with altered oligomerization specificity. Of the three substitutions required to disrupt oligomerization, the role of the substitution of Leu330 with Phe is difficult to understand based on the three-dimensional structure of the wild-type p53 tetramerization domain; the other two substitutions, Ala347 with Ile and Leu348 with Met, weaken the hydrophobic interactions between the C-termini of the α-helices that stabilize the packing of the two primary dimers. The four substitutions that restore oligomerization establish novel hydrophobic interactions (substitution of Ala 353 and Gln354 with Leu) or enhance existing hydrophobic interactions (substitution of Met340 with Phe). Thus, a redistribution of hydrophobic interactions may underlie the altered oligomerization specificity of p53IND7.

EXAMPLE 3

Oligomerization Specificity

A. In Vitro Examination of Oligomerization Specificity of the IND tetramerization domain was first examined in vitro.

We have previously established that a DNA binding assay can be modified to monitor hetero-oligomerization between p53 proteins. The experimental approach takes advantage of the fact that the migration of p53-DNA complexes on native electrophoresis gels is influenced by the molecular weight of the p53 tetramer. For example, a p53 tetramer that lacks the transactivation domain (this truncation does not compromise tetramerization or DNA binding) migrates faster than full-length p53 tetramers. Hetero-tetramers of truncated and full-length p53 can be readily detected by their distinct migration, as evidenced by analysis of cotranslated truncated and full-length p53wt proteins.

Cotranslation of full-length p53IND7 [SEQ ID NO: 3] with truncated p53wt leads to a very small fraction of p53IND7 [SEQ ID NO: 3] forming hetero-oligomers with p53wt; the major fraction of p53IND forms homo-oligomers. p53IND6 [SEQ ID NO: 4], also formed mostly homo-oligomers when cotranslated with truncated p53wt. However, as demonstrated above, p53IND6 [SEQ ID NO: 4] bound DNA less efficiently than p53IND7 [SEQ ID NO: 3].

B. In vivo Evaluation of oligomerization specificity of p53IND7

For this experiment a derivative of p53IND7 was designed substituting the N-terminal 39 residues with a hemaglutinin (HA) tag. This substitution eliminates the epitope of antibody DO-1 within the N-terminus of p53 and introduces an epitope for antibody 12CA5. The epitope-tagged p53IND7 protein was expressed in U2-OS human osteosarcoma cells and its propensity to hetero-oligomerize with the endogenous wild-type p53 protein was monitored by coimmunoprecipitation. We could not detect hetero-oligomers between endogenous p53 and epitope-tagged p53IND7However, hetero-oligomers were readily detected between endogenous p53 and an epitope-tagged p53 protein containing the native p53 oligomerization domain.

C. Discussion

Determinants of oligomerization specificity have been studied extensively in the context of leucine zippers. These amphipathic coiled coils are characterized by heptad repeats of the general sequence (abcdefg)n; where a and d are hydrophobic amino acids, and b, c, e, f and g are polar or charged residues. Leucine zipper dimerization is mediated by the hydrophobic residues at positions a and d. These hydrophobic interactions are critical for stability of the dimer, but do not contribute to oligomerization specificity. Rather, specificity is determined by the residues at positions e and g. Unfavorable electrostatic interactions between the residues at positions e of one subunit and the residues at positions g of the other subunit prevent dimerization.

In contrast to leucine zippers, the oligomerization specificity of the p53 tetramerization domain can be altered by substitutions of hydrophobic residues. The differences between the structures of leucine zippers and the p53 tetramerization domain may explain why changes in oligomerization specificity were engineered by substitutions of charged residues in the case of leucine zippers versus hydrophobic residues in the case of the p53 tetramerization domain. Coiled coils have a single secondary structure element and a cylindrical hydrophobic core. The geometry of a Coiled coil dimer provides very limited flexibility for substitutions of the hydrophobic residues at the intersubunit interface without significant loss in dimer stability. In contrast, the p53 tetramerization domain contains β-strand, turn and α-helical secondary structure elements and has a globular hydrophobic core. The globular nature of the hydrophobic core provides significantly more tolerance to hydrophobic amino acid substitutions. Thus, the hydrophobic interactions between subunits can be redistributed resulting in altered oligomerization specificity.

EXAMPLE 4

Transcriptional and Tumor Suppressor Activities

Having established that the IND6 and IND7 tetramerization domains have altered oligomerization specificity and can support sequence-specific DNA binding activity in vitro, we subsequently tested their function in vivo. This was done by examining the transcriptional and tumor suppressor activities of full-length p53IND6 [SEQ ID NO: 4] and p53IND7 [SEQ ID NO: 3] proteins; both these activities are dependent on p53 oligomerization.

A. Transcription Assay

Transcriptional activity was determined by transfecting in quadruplicate Saos-2 cells with 5 mg of p53 expression and 25 mg of reporter plasmids. Alkaline phosphatase activity was determined 48 hrs later [T. Halazonetis, *Anticancer Res.*, 12:285–292 (1992)]. To determine whether the transcriptional activities of the p53 proteins were suppressed by a tumor-derived p53 mutant, Saos-2 cells were cotransfected in triplicate with 1 mg of p53 expression plasmid, 9 mg of plasmid encoding the p53Trp248 mutant or 9 mg of pSV2 plasmid without insert and 20 mg of the Ep21/TK-seap reporter plasmid.

The transcriptional activity of the p53 proteins was monitored in Saos-2 osteosarcoma cells, which lack endogenous p53 [L. Diller et al, *Mol. Cell. Biol.*, 10:5772–5781 (1990)]. Both p53IND6 and p53IND7 activated transcription from a reporter plasmid containing the p53-binding site of the p21 gene; p53IND7 was almost as active as p53wt, whereas p53IND6 was significantly less active. The weak activity of p53IND6 in the transcription activation assay parallels its weak sequence-specific DNA binding activity in vitro and probably reflects poor homo-oligomerization affinity.

B. Tumor Suppressing Activity

Tumor suppressing activity was assayed by cotransfecting Saos-2 cells in quadruplicate with 5 mg of p53 expression plasmid, 1 mg of pSV7neo, a plasmid that confers neomycin resistance [K. Zhang et al, *Proc. Natl. Acad. Sci. USA*, 87:6281–6285 (1990)], and 24 mg of pBC12/PLseap [T. Halazonetis, *Anticancer Res.*, 12:285–292 (1992)], a carrier plasmid. The transfected cells were selected for G418 resistance and two weeks later the resistant colonies were stained with crystal violet and counted. The number of G418 resistant colonies is inversely related to tumor suppressor activity. To determine whether the tumor suppressing activities of the p53 proteins were suppressed by a tumor-derived p53 mutant, Saos-2 cells were cotransfected in triplicate with 2.5 mg of p53 expression plasmid, 10 mg of plasmid encoding the p53Trp248 mutant or 10 mg of pSV2 plasmid without insert, 1 mg of pSV7neo and 16.5 mg of pBC 12/PLseap carrier plasmid.

p53IND7 [SEQ ID NO: 3] suppressed colony formation almost as efficiently as wild-type p53; whereas p53IND6 [SEQ ID NO: 4] was a weak tumor suppressor.

To determine if p53IND7 was sensitive to transdominant inhibition by tumor-derived mutants, we studied its transcriptional and tumor suppressor activities in the presence of the tumor-derived Trp248 mutant. Transcriptional activity was determined using a reporter plasmid containing the p53 site of the p21 gene, while tumor suppressor activity was determined by the colony forming assay. In both assays, the activity of p53IND7 [SEQ ID NO: 3] was only weakly inhibited by the Trp248 mutant, whereas the activity of wild-type p53 was severely inhibited.

All publications cited in this specification are individually incorporated herein by reference in the location where it is cited. While the invention has been described with reference to a particularly preferred embodiment, it will be appreciated that numerous modifications and variations of the present invention are included in the above-identified specification and are expected to be readily apparent to one of skill in the art. Such modifications and alterations to the compositions and processes of the present invention are encompassed within the scope of the claims appended hereto.

What is claimed is:

1. A modified p53 protein comprising:
   (a) p53 DNA binding domain, said domain (a) having the sequence of amino acids 93–293 of SEQ ID NO: 3; said sequence having an optional single amino acid substitution at amino acid residue 248, 273, or 284 of SEQ ID NO: 3; and
   (b) a modified p53 tetramerization domain that does not hetero-oligomerize with a wild type p53 tetramerization domain, said domain (b) having the sequence of amino acids 325 to 355 of SEQ ID NO: 3, wherein the amino acid residue 340 is Met or Phe.

2. The modified p53 protein according to claim 1, comprising amino acid residues 1–393 of SEQ ID NO: 3, wherein amino acid residue 340 is Met or Phe.

3. The modified protein according to claim 2, wherein amino acid residues 3 to 80 of SEQ ID NO: 3 are replaced by amino acid residues 402 to 479 of herpes simplex virus protein VP16.

4. The modified protein according to claim 1 comprising amino acid residues 1–355 of SEQ ID NO: 3, wherein amino acid residue 340 is Met or Phe.

5. The modified protein according to claim 1 comprising amino acid residues 1–364 of SEQ ID NO: 3, wherein amino acid residue 340 is Met or Phe.

6. The modified protein according to claim 1, wherein said DNA binding domain is amino acid 93–293 of SEQ ID NO: 3, having a single amino acid residue replacement selected from the group consisting of:
   (a) Gln at residue 248;
   (b) His at residue 273;
   (c) Cys at residue 273;
   (d) Arg at residue 284; and
   (e) Lys at residue 284.

7. A nucleic acid molecule comprising the nucleic acid sequence encoding a modified p53 protein according to claim 1.

8. The nucleic acid molecule according to claim 7, wherein said molecule further comprises regulatory sequences which direct expression of said modified tetramerization domain or modified p53 protein.

9. A vector comprising a nucleic acid sequence according to claim 7 and sequences which direct expression thereof.

10. A composition comprising a nucleic acid sequence according to claim 7.

11. A composition comprising:
   (a) a modified p53 protein comprising:.
      (1) a p53 DNA binding domain, said domain (1) having the sequence of amino acids 93–293 of SEQ ID NO: 3, said sequence having an optional single amino acid substitution at amino acid residue 248, 273, or 284 of SEQ ID NO: 3; and
      (2) a modified p53 tetramerization domain that does not hetero-oligomerize with a wild type p53 tetramerization domain, said domain (2) having the sequence of amino acids 325 to 355 of SEQ ID NO: 3, wherein amino acid residue 340 is Met or Phe; and
   (b) a carrier.

* * * * *